(12) United States Patent
Neji

(10) Patent No.: US 10,139,463 B2
(45) Date of Patent: Nov. 27, 2018

(54) METHOD AND APPARATUS TO DETERMINE COMPLEX SENSITIVITY FACTORS OF RF RECEPTION COILS FOR MAGNETIC RESONANCE SPECTROSCOPY

(71) Applicant: Siemens Aktiengesellschaft, Munich (DE)

(72) Inventor: Radhouene Neji, London (GB)

(73) Assignee: Siemens Aktiengesellschaft, Munich (DE)

( * ) Notice: Subject to any disclaimer, the term of this patent is extended or adjusted under 35 U.S.C. 154(b) by 866 days.

(21) Appl. No.: 14/713,397

(22) Filed: May 15, 2015

(65) Prior Publication Data
US 2015/0331077 A1 Nov. 19, 2015

(30) Foreign Application Priority Data

May 16, 2014 (DE) .................. 10 2014 209 364

(51) Int. Cl.
*G01R 33/56* (2006.01)
*G01R 33/34* (2006.01)
(Continued)

(52) U.S. Cl.
CPC .......... *G01R 33/5608* (2013.01); *A61B 5/055* (2013.01); *G01R 33/307* (2013.01); *G01R 33/34046* (2013.01); *G01R 33/34092* (2013.01); *G01R 33/46* (2013.01); *G01R 33/5607* (2013.01); *G01R 33/583* (2013.01); *A61B 5/0555* (2013.01); *A61B 2576/026* (2013.01); *G01R 33/4625* (2013.01); *G01R 33/483* (2013.01)

(58) Field of Classification Search
CPC .... A61B 5/055; A61B 5/0555; G01R 33/5608
See application file for complete search history.

(56) References Cited

U.S. PATENT DOCUMENTS

| | | | | |
|---|---|---|---|---|
| 2012/0119737 A1* | 5/2012 | Jellus | .................. | G01R 33/561 324/309 |
| 2012/0249138 A1* | 10/2012 | Pfeuffer | ........... | G01R 33/56563 324/309 |
| 2014/0084924 A1* | 3/2014 | Grodzki | ............... | G01R 33/565 324/309 |

OTHER PUBLICATIONS

Brown, "Time-Domain Combination of MR Spectroscopy Data Acquired Using Phased-Array Coil," Magnetic Resonance in Medicine, vol. 52, pp. 1207-1213; (2004).
(Continued)

*Primary Examiner* — Jermele M Hollington
*Assistant Examiner* — Alvaro Fortich
(74) *Attorney, Agent, or Firm* — Schiff Hardin LLP

(57) ABSTRACT

In a method for determining a complex sensitivity factor of an RF reception coil, which is part of an arrangement of a number of RF reception coils of a magnetic resonance scanner, which are operates to simultaneously acquire magnetic resonance spectroscopy data, FID signals from a volume of interest are acquired simultaneously with each of the RF reception coils, and one of the RF reception coils is designated as a reference coil and its FID signal is designated as a reference signal. A complex sensitivity factor for each other RF reception coil is determined by minimizing the differences between a number of data points of its FID signal, weighted with the complex sensitivity factor, and the corresponding data points of the FID signal of the reference coil.

14 Claims, 3 Drawing Sheets

(51) Int. Cl.
    *G01R 33/30*    (2006.01)
    *A61B 5/055*    (2006.01)
    *G01R 33/46*    (2006.01)
    *G01R 33/58*    (2006.01)
    *G01R 33/483*   (2006.01)

(56) References Cited

OTHER PUBLICATIONS

Rodgerset Al.; « Receive Array Magnetic Resonance Spectroscopy: Whitened Singular Value Decomposition (WSVD) Gives Optimal Bayesian Solution, Magnetic Resonance in Medicine, vol. 63, pp. 881-891; (2010).

Bydder, et al.:"Optimal Phased Array Combination for Spectroscopy," Magnetic Resonance Imaging, vol. 26 (6), pp. 847-850; (2008).

Schäffter, et al.; "Fast 1H Spectroscopic Imaging Using a Multi-Element Head-Coil Array," Magnetic Resonance Medicine, vol. 40, pp. 185-193; (1998).

* cited by examiner

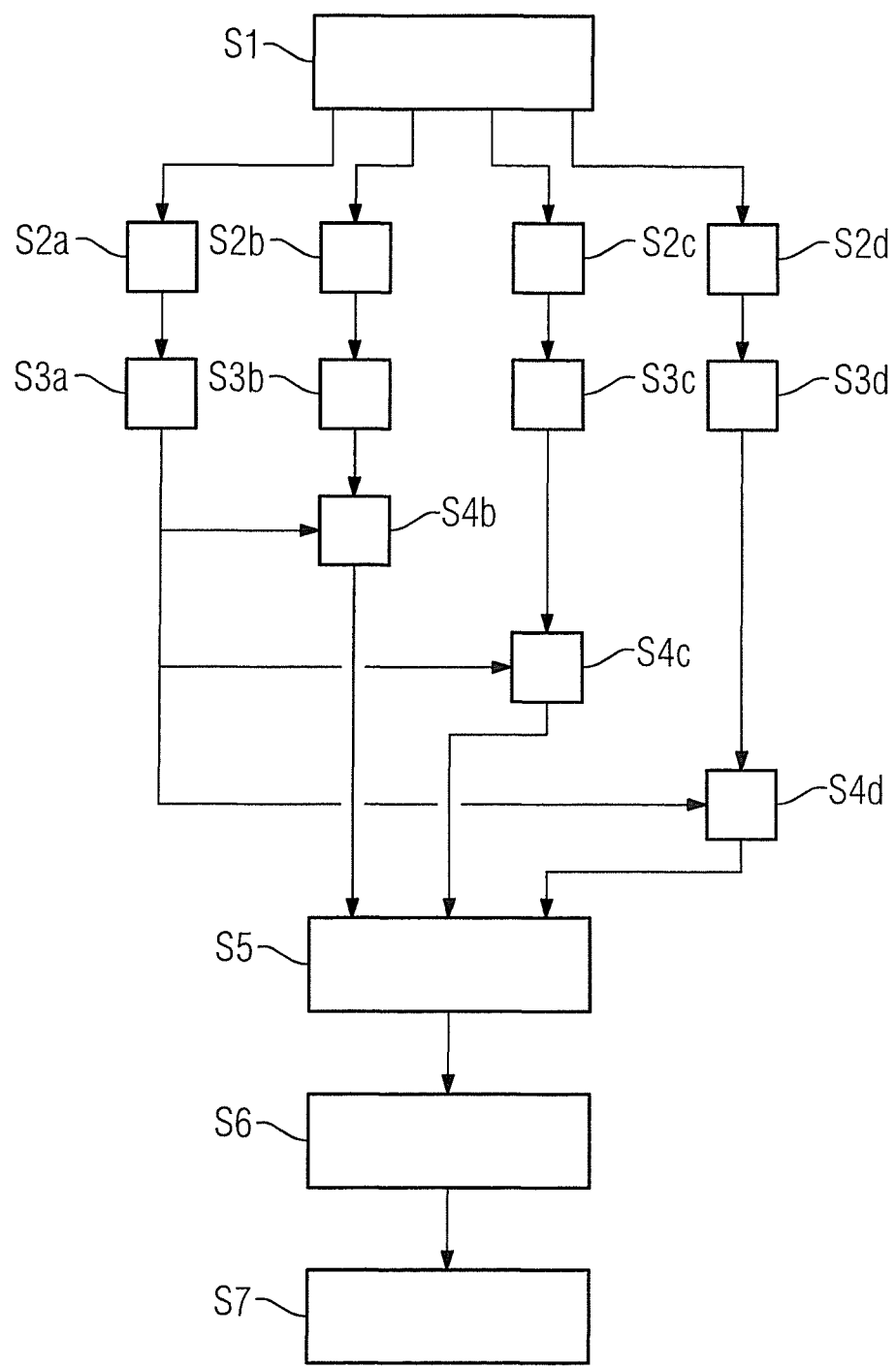

METHOD AND APPARATUS TO DETERMINE COMPLEX SENSITIVITY FACTORS OF RF RECEPTION COILS FOR MAGNETIC RESONANCE SPECTROSCOPY

BACKGROUND OF THE INVENTION

Field of the Invention

The invention relates to a method for creating a magnetic resonance spectroscopy data record for a volume of interest using a magnetic resonance unit with at least two RF reception coils, and a method for determining a complex sensitivity factor of an RF reception coil, which is part of an arrangement made up of a number of RF reception coils.

The invention also concerns a magnetic resonance apparatus, which is configured to execute the method, as well as a non-transitory, computer-readable data storage medium encoded with programming instructions for implementing such a method.

Description of the Prior Art

In magnetic resonance tomography (MRT) it is frequently advantageous not to acquire the MR signal using a large radio-frequency (RF) receive coil but using an arrangement—also referred to as an array or phased array—composed of a number of RF reception coils. These can often be arranged directly on the body of the patient and therefore have a high signal to noise ratio (SNR). Combining the signals acquired simultaneously by the different array coils to form a composite signal is not simple, however, because the process has to take into account the different sensitivity profiles of the individual coils in order to compensate for spatial intensity variations. With magnetic resonance spectroscopy (MRS) it is important to weight the contributions of the individual coils with the correct sensitivity factor for each voxel, because otherwise the SNR suffers, and spectra from different voxels cannot be compared, so it is impossible to ascertain any spatial variation in the concentration of metabolites. The sensitivity profiles of the coil arrangements should be calculated anew in each instance before a measurement on the patient, because they can vary significantly due to the individual positioning of the coil arrangement on the patient.

Different approaches are known for calculating the sensitivity profiles of the individual coil elements of an arrangement composed of RF reception coils. In the article by M. A. Brown "Time Domain Combination of MR Spectroscopy Data Acquired Using Phased-Array Coils", Magnetic Resonance in Medicine, 52:1207-1213 (2004) a method is described in which the first point of the free induction decays (FIDs) of the signals acquired with the different RF coils is used and the sensitivity factors are calculated therefrom. However this method produces flawed results when the spectra are very noisy.

In the article by T. Schäffter, P. Börnert et al. "Fast $^1H$ Spectroscopic Imaging Using a Multi-Element Head-Coil Array", Magnetic Resonance in Medicine, 40:185-193 (1998) a method is described in which the sensitivity profiles are calculated by means of a set of calibration images, which is acquired using both the coil arrangement and the body coil serving as reference. However, this requires prior measurement.

C. T. Rodgers and M. D. Robson in "Receive Array Magnetic Resonance Spectroscopy: Whitened Singular Value Decomposition (WSVD) Gives Optimal Bayesian Solution", Magnetic Resonance in Medicine, 63:881-891 (2010) propose a singular value decomposition (SVD) to determine the complex sensitivities. This approach is relatively complex.

SUMMARY OF THE INVENTION

An object of the invention is to provide a method for magnetic resonance spectroscopy using a number of RF reception coils, which is precise and does not extend the duration of the examination. It is also an object of the invention to provide a simple and fast method for determining the complex sensitivity factors of the individual RF reception coils within an arrangement or array that are of relevance for the volumes of interest selected in a specific measurement.

In the inventive method, FID (free induction decay signals) representing magnetic resonance spectroscopy data are first acquired simultaneously from the volume of interest with each of the RF reception coils. Conventionally, the person to be examined has typically been supported in the magnetic resonance unit and an arrangement composed of RF reception coils has been positioned on his/her body. The measurement here is preferably not a phantom measurement for example but an in vivo measurement or even the actual desired measurement. A $^1H$ spectroscopy is preferably performed but the method can also be used for other nuclei such as $^{13}C$, $^{31}P$ or $^{19}F$.

The FID signals are acquired from at least one volume of interest so they are preferably recorded using a location-selective MRS sequence. This can be a sequence for selecting an individual volume of interest (single voxel spectroscopy—SVS), such as PRESS or STEAM for example. Alternatively it can also be a chemical shift imaging data record, in which the signal is phase-encoded in two or three spatial directions so that individual spectra can be obtained from a plurality of voxels or volumes of interest. In this instance the method described in the following is executed individually for each voxel. To this end, the raw data are first Fourier transformed in the spatial directions, so that there is an FID signal present for each voxel or each volume of interest.

An advantage of the invention is that it operates with the signals in the time domain, in other words the FID signals. There is therefore no need for the post-processing steps required for spectrum analysis, such as phase correction, etc., which in turn could result in errors in the result.

In the inventive method, therefore, an FID signal originating from the same volume is acquired simultaneously with each of the RF reception coils and compares these in order to determine the respective complex sensitivity factors of the individual RF reception coils with respect to the volume. In this process one of the RF reception coils is first selected as a reference coil and its FID signal is designated as the reference signal. A coil with a good SNR is preferably selected as the reference coil.

A complex sensitivity factor is then determined for each RF reception coil apart from the reference coil. This factor represents the complex sensitivity of the respective RF reception coil in relation to the reference coil. The factor is a complex number so it has phase and amplitude.

The complex sensitivity factor is determined by minimizing the differences between a number of data points of the respective FID signal, weighted with the (initially unknown) complex sensitivity factor, and the corresponding data points of the reference signal. The inventive method is characterized by not using just use one data point, but rather a number or even all of the data points of the FID signals, and is therefore very exact and robust.

The already-acquired FID signals can then be weighted with the determined complex sensitivity factors and brought together to produce a usable magnetic resonance spectroscopy data record.

A further advantage of the inventive method is that the actual measurement can be used to determine the sensitivity profiles or the complex sensitivity factors of the individual RF reception coils. There is no need for additional calibration measurement.

Alternatively or additionally, the complex sensitivity factors can be used to weight further magnetic resonance spectroscopy data acquired simultaneously from the volume of interest by the RF reception coils. For example the original measurement can be repeated using a slightly different sequence but from the same volume of interest.

The steps cited above are repeated for the FID signals associated with each volume of interest, where a number of volumes of interest are present, for example in a CSI data record.

According to a preferred embodiment the complex sensitivity factors are determined by minimizing the $L^2$ norm between the reference signal and the FID signal of the respective RF reception coil, weighted with its complex sensitivity factor. The $L^2$ norm is also referred to as the Euclidean norm or Euclidean distance. If we consider for example the distance between two points in three-dimensional space, where the first point has the coordinates $(x_1, y_1, z_1)$ and the second point the coordinates $(x_2, y_2, z_2)$, the $L^2$ norm between the points is $\sqrt{(x_2-x_1)^2+(y_2-y_1)^2+(z_2-z_1)^2}$. This calculation can now be envisaged for an N-dimensional space, where N is the number of data points of the FID signals taken into account or used for the minimization. The advantage of this type of calculation is that it is simple to implement and stable.

According to one embodiment the complex sensitivity factor of an individual RF reception coil is calculated as follows: f1(t) designates the (complex) FID signal of the reference coil (therefore the reference signal). f2(t) is the FID signal of the respective RF reception coil. The complex sensitivity factor S for f2 is to be found. According to an embodiment, the $L^2$ norm between f1(t) and S f2(t) is minimized, in other words $\|f1(t)-Sf2(t)\|^2$.

By calculating the gradient of the squared $L^2$ norm it is possible to show (intermediate steps have been omitted here) that $$S = \frac{\int_0^T f1(t)f2(t)*dt}{\int_0^T |f2(t)|^2 dt} \quad (1)$$

where f2(t)* is the complex conjugate of f2(t) and the integral takes place over the duration of the FID signal T. This formula is relatively simple to calculate. T does not have to be the total duration of the FIDs but can also cover the data points at which the FID signals are above a certain threshold value.

If the limit value of S is calculated, as T approaches 0, then $$\lim_{T \to 0} S = \frac{f1(0)f2(0)*}{|f2(0)|^2} \quad (2)$$

The amplitude of this limit value is $|f1(0)|/|f2(0)|$ and the phase is Phase (f1(0))–Phase (f2(0)). This corresponds to the solution of M. A. Brown, in which only the first points of the FIDs are used in each instance. This calculation was only performed as a control, to ensure that the calculation method used is correct. However the subject matter of the invention is not the calculation of the limit value for T→0, but the utilization of all the FID signals.

According to a further embodiment, the complex sensitivity factors are determined by minimizing the square roots of the sum of the squares of the differences between individual data points of the reference signal and the respectively corresponding data points of the FID signal of the respective RF reception coil, weighted with its complex sensitivity factor. This calculation method can correspond to the $L^2$ norm.

Many or even all of the data points of the respective FID signals are advantageously calculated when minimizing the difference. To make an expedient selection, it is possible to use for example all the data points of the respective FID signals, the value of which is above a certain threshold value. This, for example, cuts off the FID signal where the signal approaches 0 and provides no further information. Alternatively the respective FID signals can also be cut off at a previously specified time point T. Alternatively all the data of the FID signals and of the reference signal can also be used in the calculation or minimization mentioned above.

In an embodiment, the at least two RF reception coils are part of an array coil or phased array coil. However this is not essential. It is important that an arrangement of RF reception coils is present, said coils being arranged at different positions on the volume of interest and being configured to acquire MR data simultaneously, namely from at least spatially overlapping sensitive regions.

The RF reception coil, the FID signal of which has the highest signal to noise ratio, is advantageously selected as the reference coil. This has the advantage that as little noise as possible is included in the calculation of the complex sensitivity factors. This can be determined beforehand but it is also easy to calculate the SNR of the acquired FID signals, for example by taking the signal of the first point or its amplitude as signal and the mean value of the last points of the FIDs as noise.

In the case of $^1H$ spectroscopy, water suppression is undertaken during a standard spectroscopic examination. This cannot be done with many methods of the prior art, because otherwise the signal strength is too low for the determination of the sensitivity factors. The inventive method is characterized by the water-suppressed FID signals also having sufficient signal strength for the performance of the method. This is because not just one point is taken into account, but many or even all the points of the FID signals. According to one embodiment of the invention therefore water suppression is undertaken as part of the acquisition of the FID signals with magnetic resonance spectroscopy data. It can be helpful in some instances to reduce water suppression, in other words only to operate with incomplete, for example 80-98%, water suppression.

The invention also concerns a method for determining a complex sensitivity factor, as described above.

The invention also encompasses a magnetic resonance apparatus, which is configured to perform the inventive method. From the hardware point of view the apparatus can be a standard magnetic resonance system, which has a scanner with at least one gradient coil for generating a gradient field and at least two RF reception coils, each with its own reception channel, for acquiring magnetic resonance-spectroscopy data. Further components, such as a basic field magnet, an RF transmit coil, ADCs, processors, are also present, in the manner known to the person skilled in the art. The RF reception coils can also simultaneously function as transmit coils, in other words transmitting excitation pulses. However a body coil is typically used as an RF transmit coil. The control computer switches the gradient coils and controls data acquisition. The control computer is, for example, part of a console, a workstation computer, a PC, laptop, tablet computer or even a mobile device, such as a smart phone for example. The control computer is configured to cause the method to be implemented. In particular, it is able to control the magnetic resonance apparatus such that it executes the inventive method.

The magnetic resonance apparatus (i.e., the scanner thereof) can produce a basic magnetic field of 1.5 T, 2 T or even 3 T. The magnetic resonance apparatus can be, for example, an apparatus from the Siemens Magnetom series.

The present invention also encompasses a non-transitory, computer-readable data storage medium encoded with programming instructions, the storage medium being loaded into a control computer of a magnetic resonance apparatus and the programming instructions causing the control computer to operate the magnetic resonance apparatus in order to execute any or all embodiments of the method as described above.

BRIEF DESCRIPTION OF THE DRAWINGS

FIG. 5 is a flowchart of an embodiment of the inventive method.

DESCRIPTION OF THE PREFERRED EMBODIMENTS

Figure 1:
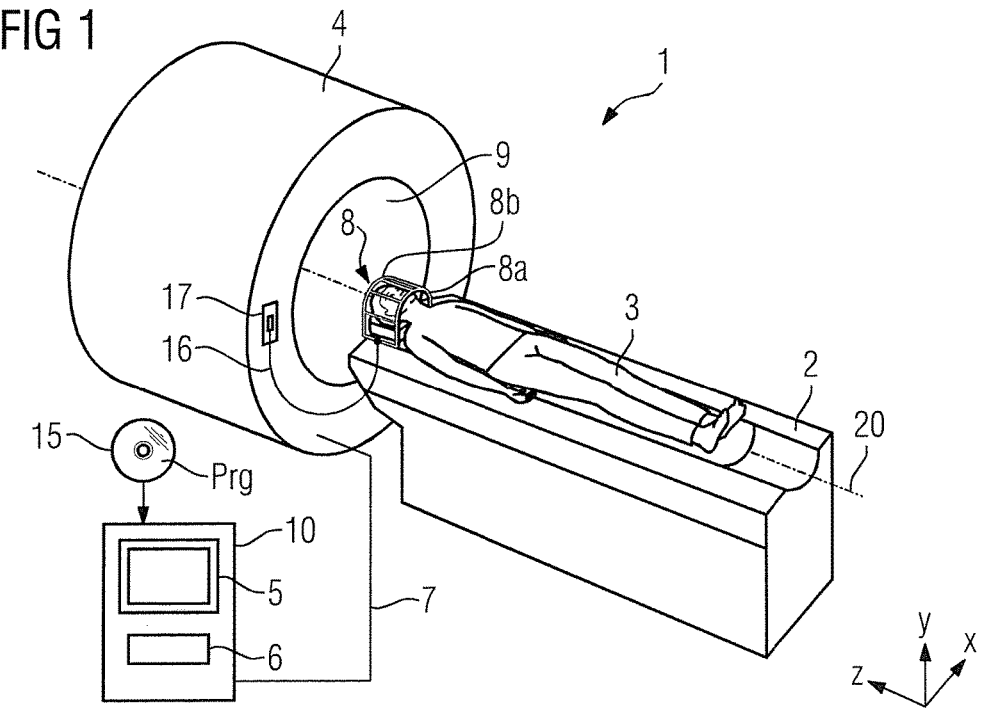
FIG. 1 is a simplified perspective view of a magnetic resonance apparatus, with which the inventive method can be executed.

With reference to FIG. 1 an inventively embodied magnetic resonance unit 1 in the illustrated embodiment has a basic field magnet 4 with an interior space 9. A patient 3 lies on a patient bed 2, which can be moved along the device axis 20 into the interior space 9.

In the illustrated example, the head of the patient 3 is in a head coil 8, in this instance composed of two separate RF reception coils 8a and 8b, each having its own receive channel. This is only one of many conceivable exemplary embodiments. More than two RF reception coils can also be provided. The arrangement of RF reception coils can also form a body coil, for example a phased array coil. Head coils composed of four RF reception coils each arranged concentrically about an axis are also conceivable.

The head coil 8 is connected by the cable loom 16 to the connector 17 and, like all the other components of the magnetic resonance unit, is controlled by the control computer 6. This is typically integrated in an operating console 10. The control facility 6 is typically part of a computer, for example the central computation unit, for example a CPU. Memory modules, for example a hard disk or RAM or other data storage units for storing predetermined values, pulse profiles, etc., can also be part of the control unit 6. The operating console 10 also has a screen 5 and optionally input means such as keyboard and mouse (not shown), allowing a user to input data. A software program, which contains program code segments Prg for performing the inventive method, can be stored on a digital storage medium 15, for example a digital, optical or magnetic data storage unit, for example a CD-ROM, and can thus be uploaded into the control computer 6.

Figure 2:
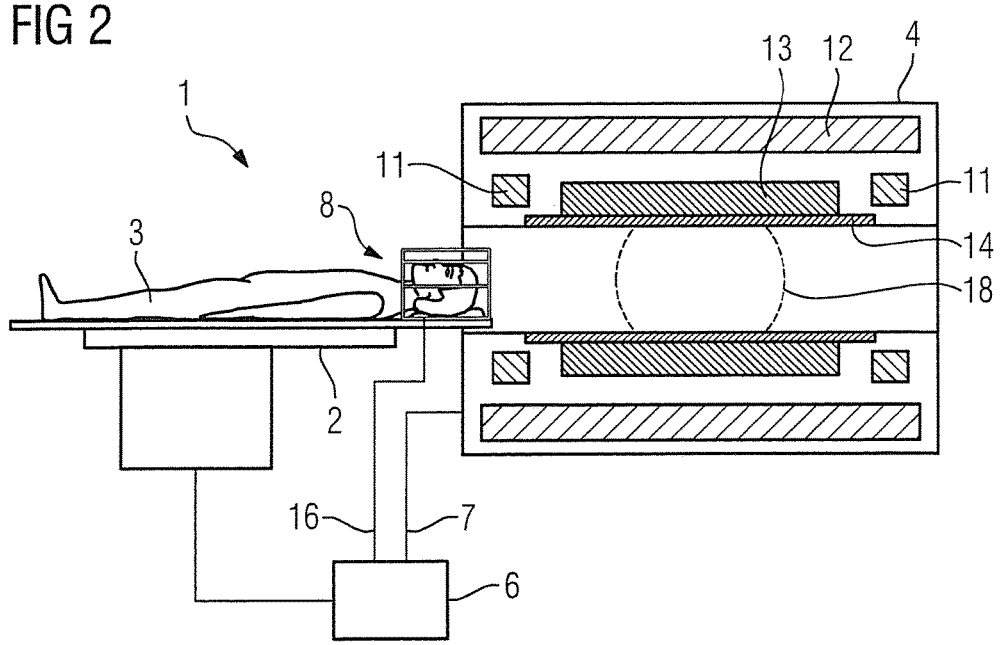
FIG. 2 is a longitudinal section through the magnetic resonance unit in FIG. 1.

FIG. 2 shows a longitudinal section of the bed 2 with the patient 3 lying thereon. The head of the patient rests in the head coil 8, which is composed of two independent RF reception coils 8a and 8b. The head coil 8 is connected to the control facility 6 by way of the cable 16. The control computer 6 also controls the other components of the magnetic resonance unit 1 via the lines 7. These include inter alia the main magnet 4. This comprises inter alia the coil 12, which generates the main magnetic field and is generally made of a superconducting material. A gradient system 13 is also present, which comprises at least one gradient coil for generating a gradient field. Shim coils 11 are also illustrated schematically. An RF whole body coil, which typically functions as a transmit coil, is shown with the reference character 14. The representation in FIG. 2 is purely schematic and the spatial arrangement of the components involved can be different from the arrangement shown. Further components of the magnetic resonance unit, for example ADCs, frequency generators, amplifiers, filters and other transducers, are not shown in this figure.

The basic field magnet 4 generates a powerful basic magnetic field, which is sufficiently homogeneous for the acquisition of magnetic resonance data in particular within the region 18.

Figure 3:
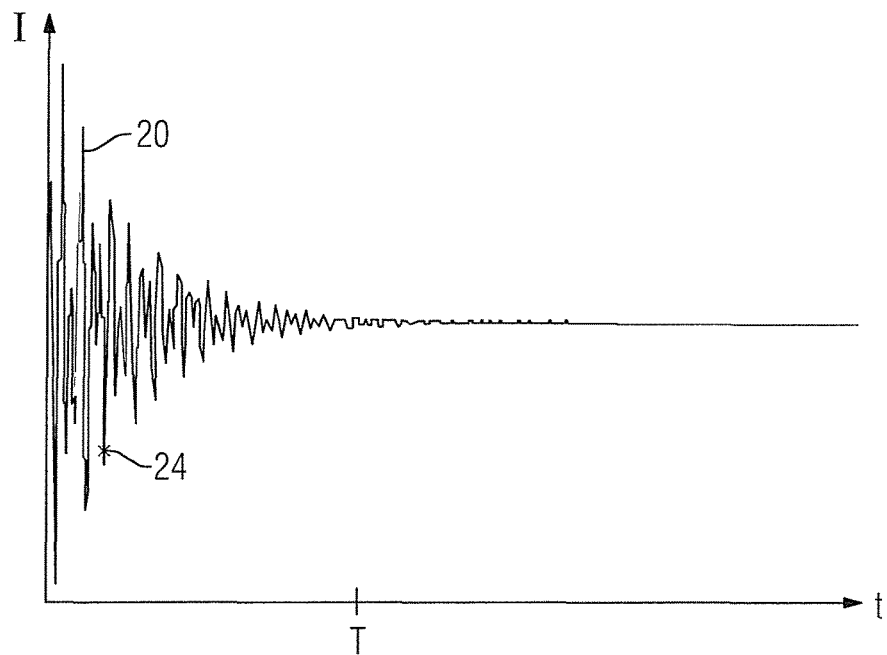
FIG. 3 shows an exemplary FID signal of a reference coil.
Figure 4:
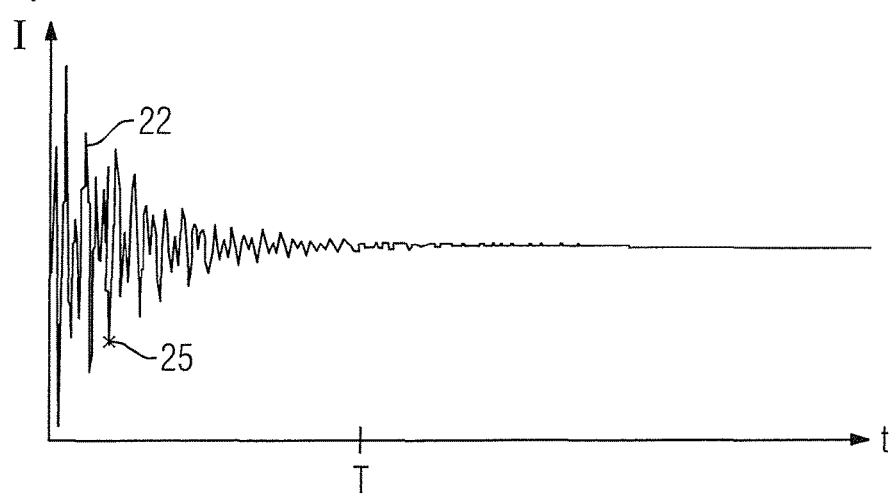
FIG. 4 shows an exemplary FID signal of another RF reception coil.

When the patient 3 has been positioned on the couch 2 and the RF transmit coils 8a, 8b have been positioned at his/her head, he/she is moved into the homogenous region 18 in the interior space 9 of the magnetic resonance unit and the measurement can start. Fast localizer images are typically recorded first, on which spectroscopy volumes can then be positioned. It is possible for example to select a layer for chemical shift imaging (CSI). Alternatively an SVS method can also be used, in which an individual volume of interest is positioned for example in the brain of the patient. The corresponding sequence for the acquisition of magnetic resonance spectroscopy data is then executed and FID signals are acquired accordingly. FIG. 3 shows an example of the FID signal received with one of the RF reception coils, the reference coil. In the case of CSI this is the FID signal to be assigned to a specific voxel. In comparison FIG. 4 shows an FID signal 22 acquired simultaneously by a different RF reception coil. Overall this has less intensity, in other words the sensitivity of this RF reception coil is probably lower for this volume of interest. Both FID signals are complex signals, in other words the drawings only show the real or imaginary part.

With the inventive method the corresponding data points on the two FID signals 20, 22 are now related to one another in order to calculate a complex sensitivity factor S. This is then used to multiply all the data points of the FID signal 22 in order to obtain a signal that is as similar as possible to the reference signal 20. For clarification two corresponding data points are shown, namely point 24 on the reference signal 20 and point 25 on the FID signal 22.

According to one embodiment the complex sensitivity factor is calculated according to the formula 1 set out above. The respective integrals can be performed up to the marked value T, at which time point the exponential decay of the FID signals has already progressed so far that essentially noise can be shown thereafter.

The general sequence of an exemplary embodiment of the inventive method is now illustrated with reference to FIG. 5. First an arrangement of RF reception coils of a magnetic resonance unit is positioned on a person to be examined. In a step S1 a sequence for acquiring MRS data is run through, as described above. In steps S2a-S2d the—in this instance four—RF reception coils therefore receive magnetic resonance spectroscopy data simultaneously from the volume of interest in the form of FID signals. In steps S3a-S3d the SNR of each FID signal is calculated, for example by determining an average value of the first data points and the last data points and dividing the same. The RF reception coil with the highest SNR is selected as the reference coil, in this instance the coil a. In steps S4b-S4d the FID signals of the RF reception coils b, c and d are then compared respectively with the reference signal, in other words the FID signal of the coil a, and the Euclidean distance of the data is minimized, weighted by a complex sensitivity factor, for example using the formula 2. The complex sensitivity factors thus calculated are buffered in step S5. The sensitivity factor 1 applies automatically for the reference coil a. In step S6 the FID signals recorded in S2a-S2d, weighted with the respective complex sensitivity factors, are brought together to provide a magnetic resonance spectroscopy data record. This can then optionally be processed further in step S7, being in particular filtered, Fourier transformed, phase corrected and optionally processed still further. It is also possible to analyze the spectrum, for example by calculating the integrals below individual peaks.

The sequence used to acquire the magnetic resonance spectroscopy data, in other words a CSI sequence or an SVS sequence, typically includes a water suppression. This can be for example an excitation pulse specific to the chemical shift of the water signal, followed by spoiler gradients. However other methods are also known for reducing or suppressing the water signal in a $^1$H magnetic resonance spectrum.

Although modifications and changes may be suggested by those skilled in the art, it is the intention of the inventor to embody within the patent warranted hereon all changes and modifications as reasonably and properly come within the scope of the inventor's contribution to the art.

I claim as my invention:

1. A method for generating a magnetic resonance (MR) spectroscopy data record for a volume of interest of an examination subject comprising:
   (a) operating an MR scanner, comprising at least two radio-frequency (RF) reception coils, from a control computer while an examination subject is situated in the MR scanner, to acquire respective free induction decays (FID) signals, representing MR spectroscopy data, from a volume of interest of the examination subject simultaneously with each of said RF reception coils;
   (b) in said control computer, selecting one of said RF reception coils as a reference coil and designating the respective FID signal thereof as a reference signal;
   (c) in said control computer, for each RF reception coil other than said reference coil, determining a complex sensitivity factor by minimizing a difference between a number of data points of the respective FID signal thereof, weighted with said complex sensitivity factor, and corresponding data points of the FID signal of the reference coil;
   (d) in said control computer, combining MR spectroscopy data acquired from said volume of interest simultaneously with said RF reception coils, weighted with the respective complex sensitivity factors, to produce an MR spectroscopy data record for said volume of interest; and
   (e) from said control computer, making said MR spectroscopy data record available in electronic form as a data file.

2. A method as claimed in claim 1 comprising, in said control computer, determining said complex sensitivity factors by minimizing an $L^2$ norm between said reference signal and the respective FID signal of the respective other RF reception coil, weighted with the respective complex sensitivity factor thereof.

3. A method as claimed in claim 1 comprising determining said complex sensitivity factors in said control computer by minimizing the square root of a sum of squares of said difference.

4. A method as claimed in claim 1 comprising selecting a number of said other RF reception coils for which the respective differences are minimized.

5. A method as claimed in claim 1 comprising minimizing only said differences that have a value above a predetermined threshold value.

6. A method as claimed in claim 1 comprising using, as said at least two RF reception coils, at least two RF reception coils that are among an RF coil array of said MR scanner.

7. A method as claimed in claim 1 comprising repeating steps (a) thru (d) for respectively different volumes of interest.

8. A method as claimed in claim 7 comprising repeating steps (a) thru (d) for all voxels in a chemical shift imaging data record.

9. A method as claimed in claim 1 comprising operating said MR scanner from said control computer to acquire said FID signals using a sequence wherein said volume of interest is individually selected.

10. A method as claimed in claim 1 comprising, in said control computer, selecting the Rf reception coil as said reference coil that has an FID signal that has a highest signal-to-noise ratio among all of the respective FID signals of said at least two RF reception coils.

11. A method as claimed in claim 1 wherein said MR spectroscopy data are $^1$H data, and, from said control computer, operating said MR scanner with water suppression during acquisition of said FID signals.

12. A method for determining a complex sensitivity factor of a radio-frequency (RF) reception coil of a magnetic resonance (MR) scanner that comprises a plurality of RF reception coils, comprising:
   (a) operating an MR scanner, comprising at least two radio-frequency (RF) reception coils, from a control computer while an examination subject is situated in the MR scanner, to acquire respective free induction decays (FID) signals, representing MR spectroscopy data, from a volume of interest of the examination subject simultaneously with each of said RF reception coils;
   (b) in said control computer, selecting one of said RF reception coils as a reference coil and designating the respective FID signal thereof as a reference signal;
   (c) in said control computer, for each RF reception coil other than said reference coil, determining a complex sensitivity factor by minimizing a difference between a number of data points of the respective FID signal thereof, weighted with said complex sensitivity factor, and corresponding data points of the FID signal of the reference coil; and (d) from said control computer, making the determined complex sensitivity factor available as an electronic signal for further processing.

13. A magnetic resonance (MR) apparatus comprising:
an MR scanner comprising a plurality of radio-frequency (RF) reception coils;
a control computer configured to operate said MR scanner while an examination subject is situated in the MR scanner, to acquire respective free induction decays (FID) signals, representing MR spectroscopy data, from a volume of interest of the examination subject simultaneously with each of said RF reception coils;
said control computer configured to select one of said RF reception coils as a reference coil and to designate the respective FID signal thereof as a reference signal;
said control computer, for each RF reception coil other than said reference coil, being configured to determine a complex sensitivity factor by minimizing a difference between a number of data points of the respective FID signal thereof, weighted with said complex sensitivity factor, and corresponding data points of the FID signal of the reference coil;
said control computer being configured to combine MR spectroscopy data acquired from said volume of interest simultaneously with said RF reception coils, weighted with the respective complex sensitivity factors, to produce an MR spectroscopy data record for said volume of interest; and
said control computer being configured to make said MR spectroscopy data record available in electronic form as a data file.

14. A non-transitory, computer-readable data storage medium encoded with programming instructions, said storage medium being loaded into a control computer of a magnetic resonance (MR) apparatus that comprises an MR scanner having a plurality of radio-frequency (RF) reception coils, said programming instructions causing said control computer to:
operate said MR scanner while an examination subject is situated in the MR scanner, to acquire respective free induction decays (FID) signals, representing MR spectroscopy data, from a volume of interest of the examination subject simultaneously with each of said RF reception coils;
select one of said RF reception coils as a reference coil and designate the respective FID signal thereof as a reference signal;
for each RF reception coil other than said reference coil, determine a complex sensitivity factor by minimizing a difference between a number of data points of the respective FID signal thereof, weighted with said complex sensitivity factor, and corresponding data points of the FID signal of the reference coil;
combine MR spectroscopy data acquired from said volume of interest simultaneously with said RF reception coils, weighted with the respective complex sensitivity factors, to produce an MR spectroscopy data record for said volume of interest; and
make said MR spectroscopy data record available in electronic form as a data file.

* * * * *